United States Patent [19]

Ullrich et al.

[11] Patent Number: 5,451,596
[45] Date of Patent: Sep. 19, 1995

[54] CYCLOALKYL AMINE BIS-ARYL SQUALENE SYNTHASE INHIBITORS

[75] Inventors: John W. Ullrich, Philadelphia; Terence J. Kiesow, Pottstown; Kent W. Neuenschwander, Schwenksville; Keith S. Learn, Perkiomenville; William P. Dankulich, Collegeville; Anthony C. Scotese, King of Prussia, all of Pa.

[73] Assignee: Rhone Poulenc Rorer Pharmaceuticals Inc., Collegville, Pa.

[21] Appl. No.: 997,818

[22] Filed: Dec. 29, 1992

[51] Int. Cl.$^6$ ............ A61K 31/42; C07D 263/56
[52] U.S. Cl. ............ 514/375; 548/217; 548/219; 548/156; 548/169; 548/235; 548/478; 546/176; 549/55; 549/362; 549/440; 549/407; 544/238
[58] Field of Search ............ 514/395; 548/217; A61K 31/42

[56] References Cited

U.S. PATENT DOCUMENTS

| | | |
|---|---|---|
| 4,447,611 | 5/1984 | Klaubert et al. . |
| 4,681,883 | 7/1987 | Brown et al. . |
| 4,826,838 | 5/1989 | Richardson ............ 548/455 |
| 5,053,425 | 10/1991 | Bartizal et al. . |
| 5,055,487 | 10/1991 | Bartizal et al. . |
| 5,091,500 | 2/1992 | Lysenko et al. . |
| 5,135,935 | 8/1992 | Alberts, et al. . |

FOREIGN PATENT DOCUMENTS

| | | |
|---|---|---|
| WO92/12144 | 7/1992 | WIPO . |
| WO92/15579 | 9/1992 | |
| WO-09115 | 5/1993 | WIPO . |

OTHER PUBLICATIONS

Merck Index, 10th ed., p. 880 (1983).
J. Am. Chem. Soc. Vol. 104, No. 25, pp. 7376–7378 (1982), Sandifer, Thompson, Baughan, Poulter, Squalene Synthetase. Inhibition by an Ammonium Analogue of a Carbocationic Imtermediate in the Conversion, English Original.
J. Am. Chem. Soc. vol. 111, No. 10, pp. 3734–3739 (1989), Poulter, Capson, Thompson, Bard, Squalene Synthetase. Inhibition by Ammonium Analogues of Carbocationic Intermediates in the, English Original.
J. Med. Chem. vol. 31, No. 10, pp. 1869–1871 (1988), Biller, Forster, Gordon, Harrity, Scott, Ciosek, Jr., Isoprenoid (Phosphinylmethyl) phosphonates as Inhibitors of Squalene Synthetase, English Original.
J. Pharm. Sci., vol. 80, No. 8, pp. 785–789 (Aug. 1991), Sterling, Doukas, Ricciardi, O'Neill, Quaternary and Tertiary Quinuclidine Derivatives as Inhibitors of Choline Uptake, English Original.

*Primary Examiner*—Donald D. Daus
*Attorney, Agent, or Firm*—James A. Nicholson; Masrtin F. Savitzky; Raymond S. Parker

[57] ABSTRACT

This invention relates to a class of novel polycyclic compounds containing a cycloalkyl ring having substituted thereon a primary amine and which is further linked or bridged to two mono- and/or bicyclic rings and which reduces levels of serum cholesterol in the body without significantly reducing mevalonic metabolite synthesis. This invention relates also to pharmacological compositions and method of treatment for lowering serum cholesterol levels using the compounds of this invention.

22 Claims, 1 Drawing Sheet

CYCLOALKYL AMINE BIS-ARYL SQUALENE SYNTHASE INHIBITORS

FIELD OF THE INVENTION

The present invention relates to a class of novel compounds useful in the treatment of diseases associated with undesirable cholesterol levels in the body, and particularly diseases of the cardiovascular system, such as atherosclerosis.

Only about 7% of the total body cholesterol circulates in the plasma, where it has been linked to atherosclerosis. The remaining 93% is located in cells, where it performs vital structural and metabolic functions. Excluding the diet, which accounts for approximately one-third of the total body cholesterol, the cells obtain the necessary cholesterol by endogenous biosynthesis (FIG. 1) or by removing low density lipoprotein (LDL) from the bloodstream. Approaches to the control of plasma cholesterol levels have been varied, however it has been shown that inhibiting endogenous cholesterol biosynthesis forces the cell to rely more on LDL uptake to satisfy their cholesterol requirements. Increased LDL uptake by cells, especially liver cells, has been shown to lower plasma cholesterol levels.

Squalene synthase is a microsomal enzyme that catalyzes the reductive dimerization of two molecules of farnesyl diphosphate to form squalene. While farnesyl diphosphate serves as the precursor to several other biologically important compounds, squalene is utilized only for cholesterol biosynthesis. Consequently, this is the first totally committed step in the biosynthesis of cholesterol (see FIG. 1). Inhibition at this step would stop only de novo cholesterol synthesis while allowing other essential pathways to isopentenyl tRNA, the prenylated proteins, ubiquinone, and dolichol to proceed unimpeded.

Inhibition of HMG-CoA reductase, an enzyme positioned early in the cholesterol biosynthetic pathway, results in a decrease of de novo cholesterol biosynthesis and an accompanying up-regulation of LDL receptors. However due to a large induction in the amount of the HMG-CoA reductase enzyme, the effect of this inhibition is blunted somewhat and the maximum LDL cholesterol reductions attainable are limited. Since inhibition of squalene synthase does not cause the same amount of enzyme induction (HMG-CoA reductase or squalene synthase), it causes in a greater reduction of de novo cholesterol biosynthesis. This translates into more up-regulation of LDL receptors than is seen with an HMG-CoA reductase inhibitor and greater efficacy for lowering circulating LDL levels.

Reported Developments

The literature describes the cholesterol biosynthetic pathway and possible means for the inhibition of squalene synthase. In a series of papers including J. Am. Chem. Soc., 1982, 104, 7376–7378 and J. Am. Chem. Soc., 1989, 111, 3734–3739, C. Dale Poulter, et al disclose that ammonium substituted cyclopropyl polyene compounds mimic the topological and electrostatic properties of the primary cation and tertiary cation of presqualene diphosphate and in the presence of phosphate buffer, inhibit squalene synthase. Scott A. Biller et al in J. Med. Chem., 1988, 31, 1869–1871 disclose that a series of stable, non-ionizable analogues of farnesyl diphosphate, comprising phosphomethylene phosphate polyene compounds, inhibit squalene synthase.

International Patent Application published under the Patent Cooperation Treaty having International Publication Number: WO 92/15579 and assigned to the same assignee as the present application, is directed to multicyclic tertiary amine polyaromatic squalene synthetase inhibitors. These compounds all contain a multicyclic ring having a nitrogen atom therein.

U.S. Pat. No. 5,135,935 assigned to Merck and Co., is directed to squalene synthetase inhibitors which are aryl-oxadiazole-quinuclidines. International Patent Applications published under the Patent Cooperation Treaty having International Publication Numbers: WO 92/12159, 92/12158, 92/12157, 92/12156 and 92/12160 and being assigned to Glaxo Group Ltd. are directed to bridged cyclic ketal derivatives for lowering the level of blood plasma cholesterol.

The present invention is directed to a class of novel cycloalkyl-diaryl compounds having a primary amine substituted on the cycloalkyl ring and which exhibit squalene synthase inhibition properties.

SUMMARY OF THE INVENTION

This invention comprises polycyclic compounds containing a cycloalkyl ring having substituted thereon a primary amine and which is further linked or bridged to two mono- and/or bicyclic rings. The compounds of this invention possess properties which reduce levels of serum cholesterol in the body without significantly reducing mevalonic metabolite synthesis and thus provide a therapeutic agent having fewer side effects than agents which act by inhibiting the HMG-CoA reductase enzyme. This invention relates also to pharmacological compositions and method of treatment for lowering serum cholesterol levels using the compounds of this invention.

The compounds of the present invention are described as amino cycloalkyl-bis aryl ring compounds containing two linked or bridged mono- and/or bicyclic aryl rings and are further linked or bridged to a cycloalkyl ring having a primary amine attached thereon.

More specifically, the compounds of this invention are described by the compounds of Formula I:

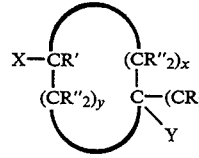 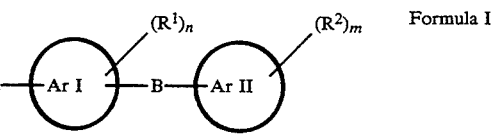

Formula I where:

a Ar I and Ar II are independently a mono- or di- aryl or heteroaryl ring;

A is O, S, NR, SO, SO$_2$, NR—C=O, O=C—NR, RC=CR, C≡C or a bond;

B is (CR$_2$)$_e$, O, S, NR, SO, SO$_2$, NR—C=O, O=C—NR, RC=CR, C≡C, O=C or a bond when Ar II is mono- aryl or heteroaryl and (CR$_2$)$_e$, O, S, O=C, NR, SO, SO$_2$ or a bond when Ar II is di- aryl or heteroaryl;

one of X or Y is R'";

one of X or Y is $H_2N-(CR_2)_z-$;
a and b are independently 0–4 and a+b=0–4;
e is 1–2;
m and n are independently 0–2;
x is 1–6;
y is 0–2;
x+y is 1–6;
z is 0–3;
R' is hydrogen, alkyl or hydroxy;
R" is hydrogen, alkyl or hydroxy;
R''' is hydrogen, alkyl, hydroxy or carboxy;
one set of vicinal R" and R''' groups may form a double bond when x+y=3–6;
R is hydrogen or alkyl;
$R^1$ and $R^2$ are independently hydrogen, alkyl, alkoxy, hydroxy, halo, haloalkyl, nitro, amino or mono- or di-alkylamino; and its stereoisomers, enantiomers, diastereoisomers and racemic mixtures; or pharmaceutically acceptable salts thereof.

DETAILED DESCRIPTION AND PREFERRED EMBODIMENTS

Figure 1:
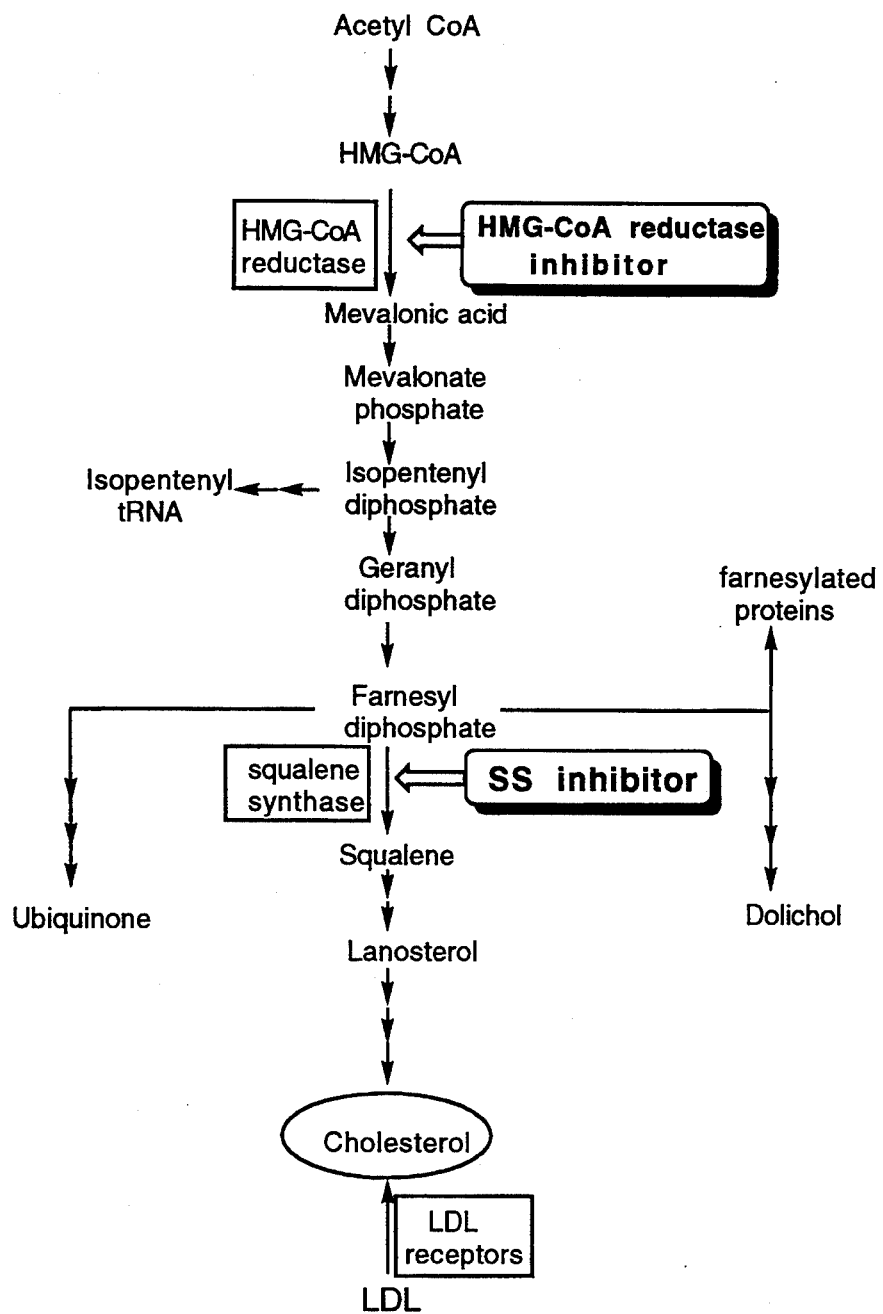
FIGURE 1 is a schematic diagram of the biosynthetic pathway of cholesterol.

As employed above and throughout this disclosure, the following terms, unless otherwise indicated, shall be understood to have the following meanings:

"Biological pH" refers to that pH of blood, plasma or serum in the body between about 7.2 and about 7.5 and which does not interfere with normal degradation of materials present therein. The normal pH of blood, plasma or serum values is about 7.35–7.45 and is preferably about pH 7.39–7.41.

"Monocyclic aryl" means a carbocyclic and/or heterocyclic aromatic ring. Preferred groups include phenyl, thienyl, pyridinyl, furyl and pyrimidinyl.

"Bicyclic aryl" means a bicyclic ring system composed of two fused carbocyclic and/or heterocyclic aromatic rings. Preferred groups include naphthyl, indolyl, benzothienyl, benzofuranyl, quinolinyl, benzoxazole and benzothiazole.

"Aryl" means a carbocyclic or heterocyclic aromatic ring.

"Alkyl" means a saturated aliphatic hydrocarbon, either branched- or straight-chained. Preferred alkyl is "loweralkyl" having about 1 to about 6 carbon atoms. Examples of alkyl include methyl, ethyl, n-propyl, isopropyl, butyl, sec-butyl, t-butyl, amyl and hexyl.

"Alkoxy" refers to an alkyl-O-group.

"Alkenyl" refers to a hydrocarbon having at least one point of unsaturation and may be branched- or straight-chained. Preferred alkenyl groups have 2 to about 6 carbon atoms. Exemplary alkenyl groups include vinyl, allyl, ethynyl and isopropenyl.

The preferred aryloxy group is phenoxy.

"Aralkyl" means an alkyl group substituted by an aryl radical. The preferred aralkyl groups are benzyl or phenethyl.

The preferred aryloxy group is phenoxy.

The preferred aralkoxy groups are benzyloxy and phenethoxy.

The preferred acyloxy group is acetoxy.

"Halo" means a halogen. Preferred halogens include chloride, bromide and fluoride. The preferred haloalkyl group is trifluoromethyl.

Preferred compounds of Formula I are defined where Ar I and Ar II are independently a substituted or unsubstituted mono- or bicyclic system of about 5 to about 14 atoms which may be partially or completely unsaturated carbocyclic or heterocyclic and where each ring of said system contains 0 to about 2 hetero atoms selected from N, O and S provided said hetero atoms are not vicinal oxygen and/or sulfur atoms and where the substituents may be located at any appropriate position of the ring system and are described by the R definition above.

Preferred monocyclic rings include aryl and unsaturated carbocyclic and heterocyclic rings. Exemplary rings are substituted or unsubstituted pyrrole, thiophene, furan, cyclopentadiene, imidazole, pyrazole, 1,2,4-triazole, pyridine, pyrazine, pyrimidine, pyridazine, thiazole, isothiazole, oxazole, isoxazole, s-triazine and benzene.

Preferred bicyclic ring systems include bicyclic aryl and bicyclic unsaturated carbocyclic and heterocyclic rings. Exemplary bicyclic rings include substituted and unsubstituted indene, isoindene, benzofuran, dihydrobenzofuran, benzothiophene, indole, 1H-indazole, indoline, imadazole; azulene, tetrahydroazulene, benzofuran, benzothiaphene, benzopyrazole, benzoimadazole, benzoxazole, benzothiazole, 1,3-benzodioxole, 1,4-benzodioxan, purine, naphthalene, tetralin, coumarin, chromone, chromene, 1,2-dihydrobenzothiopyran, tetrahydrobenzothiopyran, quinoline, isoquinoline, quinazoline, pyrido[3,4-b]-pyridine, and 1,4-benzisoxazine.

The more preferred compounds of this invention include compounds of Formulae II and III:

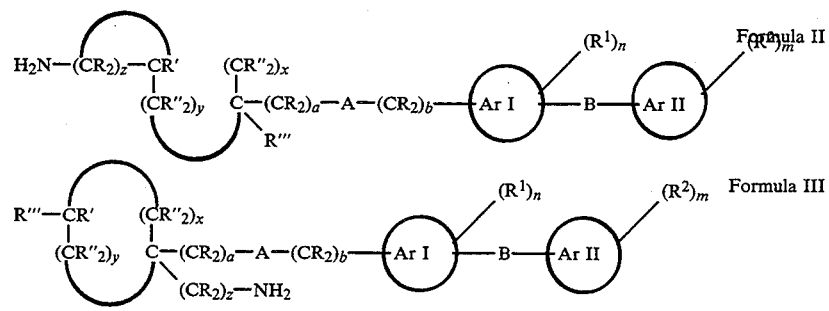

where:
Ar I is

Ar II is

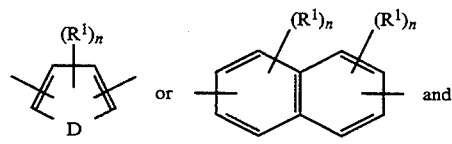

Ar II is

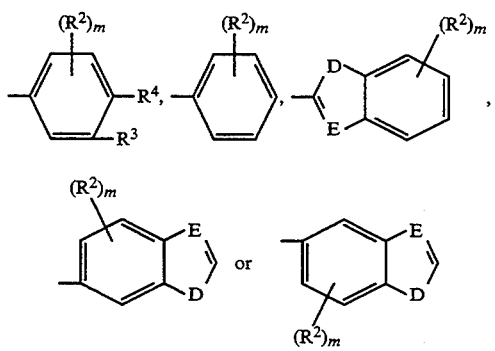

where:

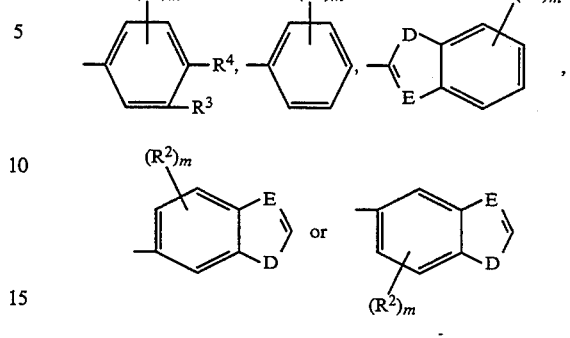

where:
D is $CH_2$, $CH=CH$, O, S or N—R;
E is CH, N or CH—O;
$R^1$ and $R^2$ are independently hydrogen, alkyl, alkoxy, hydroxy, halo or trifluoromethyl; and
$R^3$ and $R^4$ together are O—$CH_2$—$CH_2$, O—$CH_2$—$CH_2$—$CH_2$, O—$CH_2$—O or O—$CH_2$—$CH_2$—O.

A special embodiment of this invention describes those compounds of Formula IV through VII:

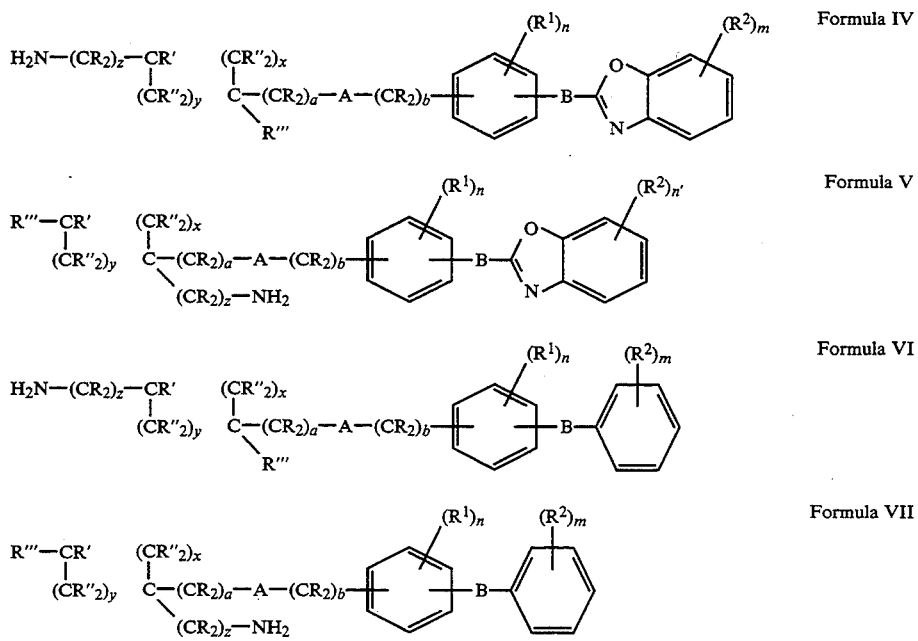

Formula IV

Formula V

Formula VI

Formula VII

D is $CH_2$, $CH=CH$, O, S or N—R;
E is CH, N or CH—O;
$R^1$ and $R^2$ are independently hydrogen, alkyl, alkoxy, hydroxy, halo or haloalkyl;
$R^3$ and $R^4$ together are O—$CH_2$—$CH_2$, O—$CH_2$—$CH_2$—$CH_2$, O—$CH_2$—O or O—$CH_2$—$CH_2$—O.

The more preferred compounds are those described by Formulae II and III where:
Ar I is

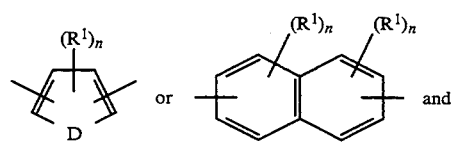

where:
A is O, S, NR, $CH=CH$ or a bond;
B is $(CR_2)_e$, O, S, NR, O=C, $CH=CH$ or a bond when Ar II is monoaryl and $(CR_2)_e$, O, S, O=C, or NR when Ar II is di-aryl;
a and b are independently 0–3 and a+b=0–3;
e is 1–2;
m and n are independently 0–2;
x is 1–6;
y is 0–2;
x+y is 1–6;
z is 0–3;
R' is hydrogen, alkyl or hydroxy;
R'' is hydrogen, alkyl or hydroxy;
R''' is hydrogen, alkyl, hydroxy or carboxy;

one set of vicinal R″ and R‴ groups may form a double bond when x+y=3–6;

R is hydrogen or alkyl; and

R¹ and R² are independently hydrogen, alkyl, alkoxy, hydroxy, halo or trifluoromethyl.

The most preferred compounds described by Formulae IV–VII include those where:

A is O or a bond;

B is CH=CH or a bond when Ar II is mono- aryl and a bond when Ar II is di- aryl;

a is 0–1;

b is 0–1;

m and n are independently 0–1;

x is 1–6;

y is 0–2;

x+y is 1–6;

z is 0–1;

R, R′, R″, R‴ and R¹ are hydrogen or hydroxy; and R² is hydrogen, alkyl, alkoxy or halo.

A special embodiment includes those compounds described by Formulae IV–V where:

A is O;

B is CH=CH or a bond when Ar II is mono- aryl and a bond when Ar II is di- aryl;

a is 0–1;

b is 0–1;

m and n are independently 0–1;

x is 1–6;

y is 0–2;

x+y is 1–6;

z is 0–1;

R, R′, R″, R‴ and R¹ are hydrogen or hydroxy; and R² is hydrogen, alkyl, alkoxy or halo.

The compounds of this invention may be prepared by employing procedures known in the literature starting from known compounds or readily preparable intermediates Exemplary general procedures are described below.

It is convenient to synthesize these molecules by employing condensation reactions at the above-described reactive A and B sites of the molecule. Exemplary general procedures are shown below and, for convenience, describe those compounds where Ar I is a benzene ring and Ar II is a benzoxazole ring. Of course, while the following reactions involved are basic to developing substituted phenyl-benzoxazole molecules having desirable substituent groups present, the substitution pattern for other mono- or bicyclic rings depends on the chemistry of the particular ring. Any such adjustments to the chemistry would be familiar to one skilled in the art.

Thus, in order to prepare those compounds where A is O, S or NR and B (CR₂)ₑ, O, S, NR, SO, SO₂, NR—C=O, O=C—NR, RC=CR, C≡C, O=C or a bond, the following reactions or combination of reactions are employed:

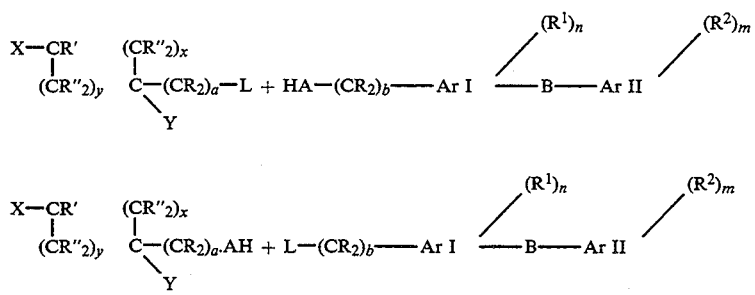

where L is a leaving group, preferably halo, tosylate or mesylate.

The amine is protected with the usual protecting groups such as phthalimide, triphenylmethyl or hydroborane complex which is removed at the appropriate time.

Where A is O or S, any base normally employed to deprotonate an alcohol or thiol may be used, such as sodium hydroxide, potassium hydroxide, sodium hydride, triethyl amine, sodium bicarbonate or diisopropylethylamine.

Reaction temperatures are in the range of −78° C. to reflux depending on the reactants involved. (Preferably about 0° C. to room temperature). Reaction times vary from about 2 to about 96 hours. The reaction is usually carried out in a solvent that will dissolve both reactants and is inert to both as well. Solvents include, but are not limited to, diethyl ether, tetrahydrofuran, N,N-dimethyl formamide, dimethyl sulfoxide, dioxane and the like.

In the case where A or B is SO or SO₂, then treatment of the thio compound with m-chlorobenzoic acid or sodium periodate results in the sulfinyl compound. Preparation of the sulfonyl compound may be accomplished by known procedures such as dissolving the sulfinyl compound in acetic acid and treating hydrogen peroxide, preferably about 30% aqueous H₂O₂.

In certain of the reaction schemes a metal salt may be used. Any appropriate metal salt formed from such as Li, K, Na, Mg, Br or the like may be used.

Those compounds where A is (CR₂)ₑ, RC=CR, O, S, C≡C, or a bond, may be prepared by one of the following reactions:

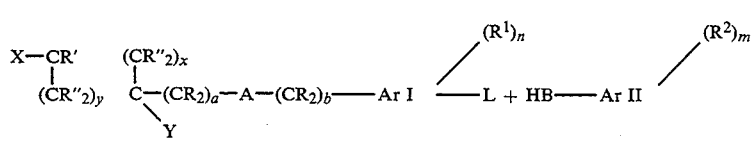

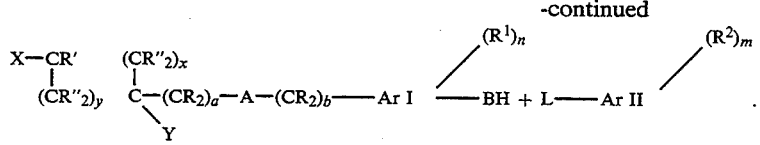

where L is a leaving group, preferably halo, tosylate or mesylate.

The amine of course, is protected by a suitable protecting group such as phthalimide, triphenylmethyl or hydroborane complex which is removed at the appropriate time. These reaction steps to protect the various substituents involved will be by known methods in the art. Further, reaction conditions may be employed as determined by the particular Ar I and Ar II rings involved as well as the presence of any reactive R″, R‴, $R^1$ or $R^2$ group.

Various substituents on the present new compounds can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups known in the art, may be employed. Examples of many of these possible groups may be found in "Protective Groups in Organic Synthesis" by T. W. Green, John Wiley and Sons, 1981. For example, nitro groups can be added by nitration and the nitro group converted to other groups, such as amino by reduction, and halo by diazotization of the amino group and replacement of the diazo group. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product.

Since the compounds of this invention have certain substituents which are necessarily present, the introduction of each substituent is, of course, dependent on the specific substituents involved and the chemistry necessary for their formation. Thus, consideration of how one substituent would be affected by a chemical reaction when forming a second substituent would involve techniques familiar to the skilled artisan. This would further be dependent on the ring involved.

Certain compounds of this invention may have at least one asymmetric carbon atom such as those compounds having different geminal groups or those compounds which contain an asymmetric carbon atom. Further, certain compounds of this invention may exist in their cis or trans configuration such as those compounds where A or B is CR=CR or R″ and R‴ form a double bond. As a result, those compounds of this invention may be obtained either as racemic mixtures, diastereoisomeric mixtures or as individual enantiomers. When two or three asymmetric centers are present the product may exist as mixtures of two or four diastereomers. Of course it is understood that certain other compounds within the scope of this invention could have a number of stereocenters. In general, a compound with x stereocenters can have a maximum of $2^x$ stereoisomers. Therefore, a compound having three such centers gives rise to a maximum of eight stereoisomers, while one having four produces sixteen, etc. The product may be synthesized as a mixture of the isomers and then the desired isomer separated by conventional techniques such as chromatography or fractional crystallization from which each diastereomer may be resolved. On the other hand, synthesis may be carried out by known stereospecific processes using the desired form of the intermediate which would result in obtaining the desired stereospecificity.

Reference to the separation of cis and trans isomers by chromatography may be found in W. K. Chan, et al, J. Am. Chem. Soc. 96, 3642, 1974.

It is to be understood that the scope of this invention encompasses not only the various isomers which may exist but also the various mixture of isomers which may be formed.

The resolution of the compounds of this invention and their starting materials may be carried out by known procedures. Incorporation by reference is hereby made to the four volume compendium *Optical Resolution Procedures for Chemical Compounds:* Optical Resolution Information Center, Manhattan College, Riverdale, N.Y. Such procedures are useful in the practice of this invention. A further useful reference is *Enantiomers, Racemates* and *Resolutions:* Jean Jacques, Andre Collet and Samuel H. Wilen; John Wiley & Sons, Inc., New York, 1981. Basically, the resolution of the compounds is based on the differences in the physical properties of diastereomers. Conversion of the racemates into a mixture of diastereomers by attachment of an enantiomerically pure moiety results in forms that are separable by fractional crystallization, distillation or chromatography.

The present compounds form salts with acids when a basic amino function is present and salts with bases when an acid function, i.e., carboxyl, is present. All such salts are useful in the isolation and/or purification of the new products. Of particular value are the pharmaceutically acceptable salts with both acids and bases. Suitable acids include, for example, hydrochloric, sulfuric, nitric, benzenesulfonic, toluenesulfonic, acetic, maleic, tartaric and the like which are pharmaceutically acceptable. Basic salts for pharmaceutical use are the Na, K, Ca and Mg salts.

The compounds of the present invention may be prepared by the following representative examples.

EXAMPLE 1

Trans-2-[4-(benzoxazol-2-yl)benzyloxy]cyclohexylamine acetate

Step A: Trans-2-(N-phthaloyl)cyclohexanol

A mixture of trans-2-aminocyclohexanol (50 g, 0.33 mol), phthalic anhydride (58 g, 0.39 mol) and triethylamine (160.8 ml, 1.15 mol) in 500 ml chloroform is stirred at reflux under nitrogen overnight. The solution is then cooled to room temperature, washed with aqueous sodium carbonate, the chloroform layer is separated, dried and concentrated in vacuo. The crude compound is passed through silica gel using ethylene chloride as eluent to obtain trans-2-(N-phthaloyl)-cyclohexanol which is used directly in the next step.

Step B:
Trans-1-[4-(benzoxazol-2-yl)benzyloxy]-2-phthaloylcyclohexane

To an activated mixture of sodium hydride (60% in mineral oil; 0.72 g, 18 mmol) in 20 ml DMF is added trans-2-(N-phthaloyl)cyclohexanol (4 g; 16.32 mmol) in 20 ml DMF, dropwise. The solution is stirred under nitrogen at room temperature for 1 hr. To this is added dropwise 4-(benzoxazol-2-yl)benzyl bromide (5.2 g; 18.00 mmol) in 16 ml DMF under nitrogen. The solution is stirred at room temperature overnight. The solution is then poured into ice/ammonium chloride/ethylacetate/hexane. The organic layer is separated, washed with $H_2O$: brine; 1:1, 5 X, dried, concentrated in vacuo and passed through a silica gel column using 0–2% MeOH:$CH_2Cl_2$ to obtain trans-1-[4-(benzoxazol-2-yl)benzyloxy]-2-phthaloyl-cyclohexane which is used directly in the next step.

Step C:
Trans-2-[4-(benzoxazol-2-yl)benzyloxy]cyclohexylamine acetate

To a mixture of trans-1-[4-(benzoxazol-2-yl)benzyloxy]-2-phthaloylcyclohexane (3.7 g; 8.18 mmol), in isopropanol (70 ml) and water (13 ml) is added sodium borohydride (1.5 g; 40.93 mmol). The solution is stirred at room temperature under nitrogen overnight. Acetic acid is then slowly added to the reaction mixture at room temperature and then the temperature of the mixture is allowed to rise to 110° C. The reaction mixture is stirred with refluxing under nitrogen overnight. The solution is then cooled to room temperature and azeotroped 6× with toluene and the evacuated. The crude material is purified over silica gel with 0–20% MeOH:$CH_2Cl_2$ and recrystalized from EtOH/hexane to obtain trans-2-[4-(benzoxazol-2-yl)benzyloxy]cyclohexylamine acetate.

EXAMPLE 2

Cis-2-[(4-benzoxazol-2-yl)benzyloxy]cyclohexylamine hydrochloride

Step A: Cis-2-triphenylmethylaminocyclohexanol

A mixture of cis-2-aminocyclohexanol hydrochloride (4.88 g; 32 mmol) (William S. Johnson and Elliot N. Schubert, *J.A.C.S.*, Vol. 72, pp. 2187–2190 (1950), triphenylmethylchloride (10.7 g; 38.4 mmol) and triethylamine ( 16 ml; 115 mmol) in 250 ml methylene chloride are refluxed for 3 hrs. then stirred at room temperature overnight. The mixture is poured into $H_2O$ and extracted with $CH_2Cl_2$ (200 ml), dried ($Na_2SO_4$) concentrated in vacuo and flash chromatographed using 9:1 7:1; hexane:EtOAc to obtain cis-2-triphenylmethylaminocyclohexanol which is used directly in the next step.

Step B:
Cis-1-[4-(benzoxazol-2-yl)benzyloxy]-2-triphenylmethylaminocyclohexane

Cis-2-triphenylmethylaminocyclohexanol (1.52 g; 4.25 mmol) is added to a solution of sodium hydride (256 mg; 60%; 6.4 mmol) in 20 ml dry THF and refluxed overnight. The solution is cooled, 4-(benzoxazol-2-yl)benzyl bromide (1.3 g; 4.5 mmol) is added in one portion and refluxed for 5 hrs. This is then poured into water and extracted with 2×100 ml $CH_2Cl_2$, dried ($Na_2SO_4$), concentrated to dryness and flash chromatographed using 4:1 8:1; hexane:EtOAc to obtain Cis-1-[4-(benzoxazol-2-yl)benzyloxy]-2-triphenylmethylaminocyclohexane which is used directly in the next step.

Step C:
Cis-2-[(4-benzoxazol-2-yl)benzyloxy]cyclohexylamine hydrochloride

Cis-1-[4-(benzoxazol-2-yl)benzyloxy]-2-triphenylmethylaminocyclohexane (2.03 g; 3.6 mmol) in 200 ml ethanol is treated with ethanolic HCl to pH 4 and stirred for 24 hrs. at room temperature. The solution is concentrated in vacuo, treated with ether and a white solid which precipitates out is filtered, washed with dry ether and dried in vacuo to obtain cis-2-[(4-benzoxazol-2-yl)benzyloxy]cyclohexylamine hydrochloride (m.p. 280°–281° C. dec).

EXAMPLE 3

2α-hydroxy-3β[(4-benzoxazol-2-yl)benzyloxy]cyclohexyl-1β-amine

2β-hydroxy-3β[(4-benzoxazol-2-yl)benzyloxy]cyclohexyl-1α-amine

Step A: 3-[3-(benzoxazol-2-yl)benzyloxy]cyclohexane

A mixture of 2-cyclohexan-1-ol (0.63 ml; 6.4 mmol) and sodium hydride (60%; 384 g; 9.6 mmol) in 30 ml dry THF is refluxed overnight. The solution is cooled and 4-(benzoxazol-2-yl)benzyl bromide (1.95 g; 6.75 mmol) is added in one portion and refluxing continued for 5 hrs. The solution is quenched with the addition of 2 ml $H_2O$, concentrated in vacuo poured into $H_2O$ and extracted with 2×100 ml $CH_2Cl_2$, dried ($Na_2SO_4$), concentrated in vacuo and flash chromatographed using 9:1 6:1; hexane:EtOAc to obtain 3-[3-(benzoxazol-2-yl)benzyloxy]cyclohexane which is used directly in the next step.

Step B:
3-(benzoxazol-2-yl)benzyloxycyclohex-1β-an-2α,3α-epoxide 3-(benzoxazol-2-yl)benzyloxycyclohex-1α-an-2α,3α-epoxide 3-[3-(Benzoxazol-1-yl)benzyloxy]cyclohexane (1.26 g; 4.1 mmol) is added to m-chloroperbenzoic acid (973 mg; 80%; 4.5 mmol) in dry methylene chloride (100 ml) at 0° C. The solution is allowed to warm slowly to room temperature and stirred overnight. The solution is then poured into $H_2O$ and extracted 2×100 ml $CH_2Cl_2$, dried ($Na_2SO_4$), concentrated in vacuo and flash chromatographed using 6:1 3:1; hexane:EtOAc to afford two products. The product having the higher RF values and weighing 0.87 g is the cis-epoxide, 3-(benzoxazol-2-yl)benzyloxy-cyclohex-1α-an-2α,3α-epoxide and that having the lower RF values and weighing 0.35 g is the trans-epoxide, 3-(benzoxazol-2-yl)benzyloxycyclohex-1β-an-2α,3α-epoxide which is verified by N M R. These products are used directly in the next steps.

Step C:
2α-hydroxy-3β[(4-benzoxazol-2-yl)benzyloxy]cyclohexyl-1β-amine 3-(Benzoxazol-2-yl)benzyloxycyclohex-1β-an-2α,3α-epoxide, (330 mg) is combined with NH₄OH (2 ml) in MeOH (8 ml) and heated in a sealed tube at 80° C. for 12 hrs. The solution is then concentrated in vacuo and subjected to flash chromatography using a gradient elution of MeOH 5% ET₃N/MeOH to afford 2α-hydroxy-3β[(4-benzoxazol-2-yl)benzyloxy]cyclohexyl-1β-amine (m.p. 147°–148° C.).

Step D:
2β-hydroxy-3β[(4-benzoxazol-2-yl)benzyloxy]cyclohexyl-1α-amine

Following the procedure of Step C, above, and replacing 3-(benzoxazol-2-yl)benzyloxycyclohex-1β-an-2α,3α-epoxide with 3-(benzoxazol-2-yl) -benzyloxycyclohex-1α-an-2α,3α-epoxide then the product prepared is 2β-hydroxy -3β[(4-benzoxazol-2-yl)benzyloxy]cyclohexyl-1α-amine.

EXAMPLE 4

Trans-2-amino-[4-(benzoxazol-2-yl)benzyloxy]cyclopentane hydrochloride

Step A: Trans-2-aminocyclopentanol

A mixture of cyclopentene oxide (4 ml; 45.84 mmol), ammonium hydroxide solution (10 ml) and 4 ml methanol are heated in a sealed tube at 80° C. overnight. The reaction mixture is cooled, concentrated in vacuo to dryness and used directly in the next step.

Step B: Trans-2-triphenylmethylaminocyclopentanol

A mixture of trans-2-aminocyclopentanol (45.84 mmol), triphenylmethylchloride (11.50 g; 41.26 mmol) and triethylamine (15.97 ml; 114.60 mmol) in 100 ml CH₂Cl₂ is refluxed overnight. The reaction mixture is cooled and concentrated in vacuo and flash chromatographed using 5:1; hexane:EtOAc to obtain trans-2-triphenylmethylaminocyclopentanol which is used directly in the next step.

Step C:
Trans-2-triphenylmethylamino-[4-(benzoxazol-2yl)benzyloxy]cyclopentane

To a mixture of trans-2-triphenylmethylaminocyclopentanol (4.76 g; 13.85 mmol), is added NaH (60%; 0.83 g; 20.78 mmol) in 100 ml THF and 20 ml DMF. This mixture is stirred for 1 hr. and then 4-(benzoxazol-2-yl)benzyl bromide (3.99 g; 13.85 mmol) is added followed by potassium iodide (pinch). The reaction mixture is stirred for 72 hrs., quenched with water, concentrated in vacuo and flash chromatographed using 9:1; hexane:EtOAc to obtain trans-2-triphenylmethylamino-[4-(benzoxazol-2-yl)benzyloxy]cyclopentane which is used directly in the next step.

Step D:
Trans-2-amino-[4-(benzoxazol-2-yl)benzyloxy]cyclopentane hydrochloride

To a mixture of trans-2-triphenylmethylamino-[4-(benzoxazol-2-yl)benzyloxy]-cyclopentane (3.67 g; 6.67 mmol)in ethanol (100 ml) and CH₂Cl₂ (20 ml) is added ethanolic HCl until pH≈2. This is stirred overnight, concentrated in vacuo, washed with CH₂Cl₂, dried under vacuum and flash chromatographed using 3:1; CH₂Cl₂:EtOH. The product is rechromatographed using 3:1; CH₂Cl₂:EtOH to obtain trans-2-amino-[4-(benzoxazol-2-yl)benzyloxy]cyclopentane hydrochloride (m.p. >200° C.).

EXAMPLE 5

Trans-3-amino-[4-(benzoxazol-2-yl)benzyloxy]cyclopentane hydrochloride

Step A:
Cis-3-[benzoxazol-2-yl]benzyloxycyclopentanol

A mixture of 1.3-cyclopentanediol (5 g; 48.6 mmol), and NaH (2.15 g; 60%; 53.8 mmol) in 100 ml dry THF is refluxed overnight. This mixture is then cooled and 4-(benzoxazol-2-yl)benzyl bromide (10 g; 48.6 mmol) is added and refluxed an additional 5 hrs. To this is added 2 ml of H₂O, concentrated, and then poured into H₂O, extracted 2×100 ml CH₂Cl₂, dried (Na₂SO₄), concentrated in vacuo and flash chromatographed using CH₂Cl₂ 5% MeOH (CH₂Cl₂) to obtain a mixture of cis and trans, cis-3-[benzoxazol-2-yl]benzyloxycyclopentanol which is rechromatographed using HPLC with 0.25% EtOH (chloroform) as eluent to obtain cis-3-[benzoxazol-2-yl]benzyloxycyclopentanol (m.p. 182°–3° C.).

Step B:
Cis-3-chloro-[4-benzoxazol-2-yl)benzyloxy]cyclopentane

A mixture of cis-3-[benzoxazol-2-yl]benzyloxycyclopentanol (0.99 g; 3.2 mmol) and thionyl chloride (0.36 ml; 4.8 mmol) in dry CH₂Cl₂ is stirred at room temperature for 72 hrs. This is then poured into water, extracted with 2×100 ml CH₂Cl₂, dried (Na₂SO₄), concentrated in vacuo and flash chromatographed using 9:1; hexane:EtOAc to obtain cis-3-chloro-[4-benzoxazol-2-yl)benzyloxy]cyclopentane which is used directly in the next step.

Step C:
Trans-3-azido-[4-(benzoxazol-2-yl)benzyloxy]cyclopentane

A mixture of cis-3-chloro-[4-benzoxazol-2-yl)benzyloxy]cyclopentane (100 mg; 0.33 ml), sodium azide (44 mg; 0.67 mmol) in 5 ml dry DMF is heated at 80° C. for 24 hrs. This mixture is then concentrated, poured into water, extracted with 2×100 ml ether, dried (Na₂SO₄), concentrated in vacuo to obtain trans-3-azido-[4-(benzoxazol-2-yl)benzyloxy]cyclopentane and used directly in the next step.

Step D:
Trans-3-amino-[4-(benzoxazol-2-yl)benzyloxy]cyclopentane hydrochloride

A mixture of trans-3-azido-[4-(benzoxazol-2-yl)benzyloxy]cyclopentane (110 mg) and 10% Pd/C (20 mg) in 30 ml of dry ethanol is submitted to Paar hydrogenation for 2 hrs. at 40 p.s.i. and room temperature. This mixture is then filtered through celite and washed with 1×100 ml dry ethanol and concentrated to obtain a white solid which is dissolved in ether and precipitated as the hydrochloride salt with ethanolic HCl, filtered, washed with cold ether, dried in vacuo to obtain trans-3-amino-[4-(benzoxazol-2-yl)benzyloxy]cyclopentane hydrochloride (m.p. 235° C.).

EXAMPLE 6

1amino-[4-(benzoxazol-2-yl)benzyloxymethyl]cyclopentane hydrochloride

Step A:
1-hydroxymethyl-1-triphenylmethylaminocyclopentane

A mixture of 1-amino-1-cyclopentanemethanol (3.00 g; 26.05 mmol) and triphenylmethylchloride (7.26 g; 26.05 mmol) in 70 ml $CH_2Cl_2$ is heated overnight. The reaction mixture is cooled and flash chromatographed twice using 5:1; hexane:EtOAc to obtain 1-hydroxymethyl-1-triphenylmethylaminocyclopentane as a thick yellow oil which is used directly in the next step.

Step B: 1-triphenylmethylamino-(4-{benzoxazol-2-yl]benzyloxymethyl)cyclopentane To a mixture of 1-hydroxymethyl-1-triphenylmethylaminocyclopentane (2.95 g; 8.25 mmol) in 100 ml of THF is added sodium hydride (60%; 0.495 g; 12.38 mmol) and allowed to stir for 1 hr. To this mixture is then added 4-(benzoxazol -2-yl)benzyl bromide (1.90 g; 6.60 mmol) and heated to reflux for 48 hrs. The reaction mixture is quenched with $H_2O$, concentrated in vacuo and flash chromatographed using 7:1; hexane:EtOAc to obtain 1-triphenylmethylamino(4-[benzoxazol-2-yl]benzyloxymethyl)cyclopentane which is used directly in the next step.

Step C:
1-amino-[4-(benzoxazol-2-yl)benzyloxymethyl]cyclopentane hydrochloride To a solution of 1-triphenylmethylamino-(4-[benzoxazol-2-yl]benzyloxymethyl)cyclopentane (1.24 g; 2.20 mmol) of 1-triphenylmethylamino-(4-[benzoxazol -2-yl]benzyloxymethyl)cyclopentane in ethanol/$CH_2Cl_2$ is added ethanolic HCl until ph≅2. This is then stirred for 72 hrs., concentrated to about one-half the volume and the white precipitate which forms is filtered to obtain 1-amino-[4-(benzoxazol-2-yl)benzyloxymethyl]cyclopentane hydrochloride (m.p. >250° C.).

EXAMPLE 7

2-(2-[4-(benzoxazol-2-yl)phenyl]trans-ethenyl)trans-cyclopropylformic acid
2-(2-[4-(benzoxazol-2-yl)phenyl]cis-ethenyl)trans-cyclopropylformic acid

Step A:
4-(benzoxazol-2-yl)benzyltriphenylphosphonium bromide

A mixture of 4-(benzoxazol-2-yl)benzyl bromide (0.6 g; 2.08 mmol) and triphenylphosphine (0.55 g; 2.08 mmol) in 40 ml benzene is refluxed for 48 hrs. The reaction mixture is cooled, the white solid which precipitates is filtered off, dried under vacuum to get 4-(benzoxazol-2-yl)benzyltriphenylphosphonium bromide and used directly in the next step.

Step B:
ethyl-2-(2-[4-(benzoxazol-2-yl)phenyl]trans-ethenyl)-trans-cyclopropylformate
ethyl-2-(2-[4-(benzoxazol-2-yl)phenyl]cis-ethenyl)trans-cyclopropylformate To a mixture of 4-(benzoxazol-2-yl)benzyltriphenylphosphonium bromide (0.5 g; 0.908 mmol) in 15 ml DMF is added sodium hydride (60%; 0.073 g; 1.82 mmol). To this, after about 30 min., is added ethyl 2-formyl-1-cyclopropane-carboxylate (0.132 ml; 1 mmol) dropwise. The color changes from orange to yellow in about 5 min. This is stirred overnight, quenched with $H_2O$, concentrated in vacuo and flash chromatographed using hexane:ethylacetate; 9:1 which separates the cis (clear oil) and trans (white solid) isomers of ethyl 2-(2-[4-(benzoxazol-2-yl)phenyl]-trans-ethenyl)trans-cyclopropylformate which are confirmed by NMR before using in the next step.

Step C:
2-(2-[4-(benzoxazol-2-yl)phenyl]cis-ethenyl)trans-cyclopropylformic acid To a mixture of ethyl 2-(2-[4-(benzoxazol-2-yl)phenyl]trans-ethenyl) trans-cyclopropylformate (0.115 g; 0.345 mmol) in 50 ml of ethanol:water; 4:1 is added lithium hydroxide monohydrate (0.017 g; 0.414 mmol) and heated at 40° C. for 7 hrs. To this is added another ½ equivalent of lithium hydroxide monohydrate and heating continued at 40° C. overnight. This reaction mixture is then cooled, concentrated in vacuo, dissolved in dil. NaOH, extracted with ethylacetate and acidified with aqueous HCl to form a white solid. The latter is filtered and dried overnight to obtain 2-(2-[4-(benzoxazol-2-yl)phenyl]cis-ethenyl) trans-cyclopropyl-formic acid (m.p. 171°–172° C.).

Step D:
2-(2-[4-(benzoxazol-2-yl)phenyl]trans-ethenyl)transcyclopropylformic acid When the procedure of Step C is followed using ethyl-2-(2-[4-(benzoxazol-2-yl)phenyl]cis-ethenyl)trans-cyclopropylformate the product obtained is 2-(2-[4-(benzoxazol-2-yl)phenyl]trans-ethenyl)trans-cyclopropylformic acid (m.p. 199°–200° C.).

EXAMPLE 8

Trans-4-(4-[benzoxazol-yl]benzyloxy)cyclohexylamine

Step A: Trans-4-triphenylmethylaminocyclohexanol

A mixture of trans-4-aminocyclohexanol hydrochloride (2.00 g; 13.19 mmol), triphenylmethyl chloride (4.41 g; 15.83 mmol) and triethylamine (6.44 ml; 46.17 mmol) in 40 ml $CH_2Cl_2$ is refluxed overnight. The solids are filtered off and the residue concentrated in vacuo. The resultant product is purified with $CH_2Cl_2$ $CH_2Cl_2$: ethylacetate (5:1) to obtain trans-4-triphenylmethylaminocyclo-hexanol which is used directly in the next step.

Step B:
Trans-4-triphenylmethylamino[4-(benzoxazol-2-yl)benzyloxy]cyclohexane To a mixture of trans-4-triphenylmethylaminocyclohexanol (3.18 g; 8.90 mmol) is 100 ml THF is added sodium hydride (60%; 0.320 g; 13.35 mmol) and this is followed by the addition of 4-(benzoxazol-2-yl)benzyl bromide after about 1 hr. The mixture is heated at reflux for 1 week, cooled, concentrated in vacuo and dissolved in about 40 ml $CH_2Cl_2$; hexane:ethylacetate (9:1 ). The solid material is filtered off and the residue flash chromatographed using hexane:ethylacetate; 7:1 to obtain trans-4-triphenylmethylamino-[4-(benzoxazol-2-yl)benzyloxy]cyclohexane as a white solid which is used directly in the next step.

Step C:
Trans-4-[4-(benzoxazol-2-yl)benzyloxy]cyclohexanolamine hydrochloride To a mixture of trans-4-triphenylmethylamino-[4-(benzoxazol-2-yl)benzyloxy]-cyclohexane (0.316 g; 0.578 mmol) in 75 ml ethanol is added ethanolic HCl to pH≅2. This is stirred overnight, cooled, concentrated in vacuo and flash chromatographed using CH$_2$Cl$_2$:EtOH; 3:1 to obtain trans-4-[4-(benzoxazol-2-yl)benzyloxy]cyclohexanol amine hydrochloride which is confirmed by NMR. (m.p. >250° C.).

EXAMPLE 9
Trans-2-(4[benzoxazol-2-yl]benzyloxy)cycloheptylamine hydrochloride

Step A: Cycloheptene oxide

To a cooled mixture of m-chloroperbenzoic acid (9.87 g; 57.19 mmol) in 125 ml CH$_2$Cl$_2$ is slowly added cycloheptene (5.00 g; 51.99 mmol). The reaction mixture is gradually allowed to warm to room temperature overnight. The mixture is filtered, wash with concentrated NaHCO$_3$ and concentrated in vacuo to obtain cycloheptene oxide as a pale yellow oil which is used directly in the next step.

Step B: Trans-2-aminocycloheptanol

In a sealed tube, cycloheptene oxide (5.44 g; 48.50 mmol)and ammonium hydroxide solution (10 ml) in 4 ml methanol is heated to 80° C. for 72 hrs. After removal of the heat, the mixture is concentrated in vacuo to obtain trans-2-aminocycloheptanol which is used directly in the next step.

Step C: Trans-2-triphenylmethylaminocycloheptanol

A mixture of trans-2-aminocycloheptanol (0.97 g; 7.74 mmol), triphenylmethyl chloride (2.16 g; 7.74 mmol) and triethylamine (2.70 ml; 19.35 mmol) are combined in about 100 ml CH$_2$Cl$_2$ and heated to reflux overnight. After removing the heat, the reaction mixture is concentrated in vacuo and flash chromatographed using hexane:ethylacetate; 9:1 to obtain trans-2-triphenylmethylaminocycloheptanol which is used directly in the next step.

Step D: Trans-2-triphenylmethylamino-[4-(benzoxazol-2-yl)benzyloxy]cycloheptanol To a mixture of trans-2-triphenylmethylaminocycloheptanol (0.71 g; 1.91 mmol) in 30 ml THF and 5 ml DMF is added sodium hydride (60%; 0.115g; 2.87 mmol). After 45 min. is added 4-(benzoxazol-2-yl)benzyl bromide and potassium iodide (pinch). The reaction mixture is stirred overnight, quenched with H$_2$O, concentrated in vacuo and flash chromatographed using exane:ethylacetate; 9:1 to obtain trans-2-triphenylmethylamino-[4-(benzoxazol-2-yl)benzyloxy]cycloheptanol as a white solid which is used directly in the next step.

Step E: Trans-2-(4-[benzoxazol-2-yl]benzyloxy)cycloheptylamine hydrochloride To a mixture of trans-2-triphenylmethylamino-[4-(benzoxazol-2-yl)benzyloxy]cycloheptanol (0.454 g; 0.784 mmol) in 50 ml ether is added ethanolic HCl. This is stirred overnight, the white precipitate is filtered off. The latter indicates the presence of some starting material by NMR and is redissolved in EtOH/CH$_2$Cl$_2$ and acidified to pH≅2. This is again stirred overnight, concentrated in vacuo and flash chromatographed using CH$_2$Cl$_2$:ethanol; 5:1 to obtain trans-2-(4-[benzoxazol-2-yl]benzyloxy)cycloheptylamine hydrochloride (m.p. 249°–250° C. dec).

EXAMPLE 10
Trans-2-aminomethyl-[4-(benzoxazol-2-yl)benzyloxymethyl]cyclopropane hydrochloride

Step A: Ethyl 2-triphenylmethylaminomethylcyclopropane-1-carboxylate

To a mixture of ethyl 2-formylcyclopropane-1-carboxylate (1.00 g; 7.03 mmol) and magnesium sulfate (0.85 g; 7.03 mmol) in 50 ml methanol is added tritylamine (1.82 g; 7.03 mmol). To this is then added sodium cyanoborohydride (0.88 g; 14.06 mmol) and stirred for 48 hrs. To this is then further added 0.20 g of ethyl 2-formylcyclopropane-1-carboxylate and stirring continued for another 72 hrs. The reaction mixture is filtered, concentrated in vacuo and flash chromatographed using hexane:ethylacetate; 9:1 to obtain ethyl-2-triphenylmethylaminomethyl-cyclopropane-1-carboxylate as a colorless oil which is used directly in the next step.

Step B: 2-triphenylmethylaminomethyl-1-hydroxymethylcyclopropane

To a mixture of lithium aluminum hydride (0.077 g; 2.04 mmol) in 10 ml THF is added ethyl 2-triphenylmethylaminomethylcyclopropane-1-carboxylate (0.714 g; 1.85 mmol) in 20 ml THF and stirred overnight. The reaction mixture is quenched with water, filtered, concentrated in vacuo and flash chromatographed using hexane:ethylacetate;3:1 to obtain 2-triphenylmethylaminomethyl-1-hydroxy-methylcyclopropane as a clear oil which is used directly in the next step.

Step C: Trans-2-triphenylmethylaminomethyl-[4-(benzoxazol-2-yl)benzyloxymethyl]cyclopropane To a mixture of 2-triphenylmethylaminomethyl-1-hydroxymethylcyclopropane (0.338 g; 0.984 mmol) in 30 ml THF and 5 ml DMF is added sodium hydride (60%; 0.059 g; 1.48 mmol) followed by 4-(benzoxazol-2-yl)benzyl bromide (0.255 g; 0.886 mmol) and a pinch of potassium iodide. This is stirred overnight, quenched with water, concentrated in vacuo and flash chromatographed using hexane:ethyl-acetate; 7:1 to obtain trans-2-triphenylmethylaminomethyl-[4-(benzoxazol-2-yl)-benzyloxymethyl]cyclopropane as a pale yellow oil which is used directly in the next step.

Step D: Trans-2-aminomethyl-[4-(benzoxazol-2-yl)benzyloxymethyl]cyclopropane hydrochloride To a mixture of trans-2-triphenylmethylaminomethyl-[4-(benzoxazol-2-yl)benzyloxymethyl]cyclopropane (0.252 g; 0.458 mmol) in 40 ml EtOH:CH$_2$Cl$_2$; 10:1 is added ethanolic HCl until pH≅2. This is stirred overnight, further ethanolic HCl is added and stirring continued another 24 hrs. The reaction mixture is then heated to reflux for 5 hrs., concentrated in vacuo and flash chromatographed using CH$_2$Cl$_2$: EtCH; 3:1 to obtain trans-2-aminomethyl-[4-(benzoxazol-2-yl)benzyloxy-methyl]cyclopropane hydrochloride as a white solid (m.p. >250° C.).

EXAMPLE 11

Trans-2-[4-(benzoxazol-2-yl)benzyloxy]cyclopentylamine acetate

Step A: Trans-2-aminocyclopentanol

A mixture of cyclopentene oxide (5.00 g; 59.44 mmol) ammonium hydroxide solution (10 ml) and 4 ml methanol are placed in a sealed tube and heated at 80° C. for 72 hrs. The reaction mixture is then concentrated in vacuo and flash chromatographed using $CH_2Cl_2$; EtOH; 1:1 to obtain trans-2-aminocyclopentanol which is used directly in the next step.

Step B: Trans-N-(2-hydroxy)cyclopropylphthalimide

A mixture of trans-2-aminocyclopentanol (6.00 g; 59.32 mmol), phthalic anhydride (10.54 g; 71.18 mmol) and triethylamine (28.94 ml; 207.62 mmol) in 80 ml $CHCl_3$ are heated at reflux for 72 hrs. The reaction mixture is then concentrated in vacuo and flash chromatographed using hexane:ethylacetate; 1:1 to obtain trans-N-(2-hydroxy)cyclopropylphthalimide which is used directly in the next step.

Step C: Trans-2-(N-phthalimido)-1-[4-(benzoxazol-2-yl)benzyloxy]cyclopentane To a mixture of sodium hydride (60%; 0.322 g; 8.06 mmol) in 15 ml THF at 0° C. is added trans-N-(2-hydroxy)cyclopropylphthalimide (1.434 g; 6.20 mmol) in 10 ml THF. After about 1 hr., 4-(benzoxazol-2-yl)benzyl bromide (1.965 g; 6.82 mmol) in 5 ml DMF is added. The reaction mixture is stirred overnight, quenched with water, concentrated in vacuo and flash chromatographed using hexane:ethyl-acetate;3:1 to obtain trans-2-(N-phthalimido)-1-[4-(benzoxazol-2-yl)benzyl-oxy]cyclopentane as a white solid which is used directly in the next step.

Step D: Trans-2-[4-(benzoxazol-2-yl)benzyloxy]cyclopentylamine acetate

To a mixture of trans-2-(N-phthalimido)-1-[4-(benzoxazol-2-yl)benzyloxy]cyclopentane (0.400 g; 0.912 mmol) in 1.4 ml water and 8 ml 2-propanol is added sodium borohydride (0.173 g; 4.56 mmol) and stirred overnight, concentrated in vacuo and flash chromatographed using $CH_2Cl_2$: EtOH; 20:1 $CH_2Cl_2$: EtOH; 15:1 to obtain an off-white solid. This material is added to 8 ml of 2-propanol and 1.4 ml water to which is added 1 ml acetic acid and heated to 80° C. for 2 hrs. Upon concentration in vacuo and flash chromatography using $CH_2Cl_2$: EtOH; 5:1 trans-2-[4-(benzoxazol-2-yl)benzyloxy]cyclopentylamine acetate is obtained (m.p. >200° C.).

EXAMPLE 12

$2\beta$-hydroxy-$3\beta$[(4-benzoxazol-2-yl)benzyloxy]cyclohexyl-$1\alpha$-amine

Step A: Syn-2,3-epoxycyclohexanol

To 2-cyclohexan-1-ol (5.0 g, 51 mmol) in 100 mL dry dichloromethane at 0° C. under argon is added in portions m-chloroperbenzoic acid (13.2 g, 61 mmol) over five minutes. The mixture is permitted to warm slowly to room temperature and is stirred overnight. Residual solid is filtered off and the supernatant washed with 2×100 mL portions of saturated sodium bicarbonate solution. The organics are dried (sodium sulfate) and concentrated. Flash chromatography (gradient elution; dichloromethane to 10% methanol: dichloromethane) affords syn-2,3-epoxycyclohexanol which is further purified by distillation [Tetrahedron Lett. 4895 (1985)] and used directly in the next step.

Step B: Syn-2-(4'-benzoxazol-2"-yl-benzyloxy)cyclohexane epoxide

To potassium hydride (2.1 g, 18.4 mmol, 35%) in 50 mL dry THF at 0° C. is added syn-2-epoxycyclohexan-1-ol (1.91 g, 16.7 mmol). The mixture is stirred at 0° C. for two hours at which point 4-benzoxazolebenzylbromide (4.81 g, 16.7 mmol) is added in one portion. The mixture is permitted to warm to room temperature and is stirred for one hour. The reaction is quenched by the addition of water and concentrated. Flash chromatography (gradient elution 6:1   3:1; hexane:ethyl acetate) affords syn-2-(4'-benzoxazol-2"-yl-benzyloxy)cyclohexane epoxide which is used directly in the next step.

Step C: $2\beta$-hydroxy-$3\beta$[(4-benzoxazol-2-yl)benzyloxy]cyclohexyl-$1\alpha$-amine 2-(4'-benzoxazol-2"-yl-benzyloxy)cyclohexane epoxide (4.22 g) is combined in a sealed tube with concentrated ammonium hydroxide solution (5 mL) and methanol (20 mL) and heated at 80° C. for 12 hours. The mixture is concentrated and subjected to flash chromatography (gradient elution methanol   5% triethylamine: methanol) to afford a white solid which is recrystalized from ethanol to obtain $2\beta$-hydroxy-$3\beta$[(4-benzoxazol-2-yl)benzyloxy]cyclohexyl -$1\alpha$-amine. (m.p. 149° C.).

EXAMPLE 13

When the above procedures are followed but the appropriate starting materials are used, then the desired compound may be obtained. A representative list of compounds which may be prepared include the following:

6-$\alpha$-hydroxy-2$\alpha$-[(4-benzoxazol-2-yl)benzyloxy]-cyclohexyl-1$\beta$-amine hydrochloride (m.p. 242°–248° C.)

trans-2-(4-[2-benzoxazolyl]-benzyloxy)cyclobutylamine hydrochloride (m.p. 151°–155° C.)

trans-2-(4-[4-chlorobenzoyl]-benzyloxy)cyclohexylamine hydrochloride (Exact mass: (M+H)+:calc.=344.1417; found=344.1400)

cis-2-(4-[2-benzoxazolyl]-benzyloxy)cyclobutylamine hydrochloride (m.p. 250°–951 ° C.)

trans-2-(4-[2-benzoxazolyl]-benzyloxy)-1,2,3,4-tetrahydre-1-naphthylamine hydrochloride (m.p. >250° C.)

trans-2-(4-[2-benzoxazolyl]-benzyloxymethyl)cyclopropyl-methylamine hydrochloride (m.p. >250° C.)

1$\beta$,2$\beta$-dihydroxy-1$\alpha$-[4-(benzoxazol-2-yl)phenyl]cyclohexyl-3$\alpha$-amine (m.p. 183°–185° C.)

2$\beta$-hydroxy-1$\beta$-[4-(benzoxazol-2-yl)benzyloxy]cyclohexyl-4$\alpha$-amine 4$\beta$-hydroxy-1$\beta$-[4-(benzoxazol-2-yl)benzyloxy]cyclohexyl-3$\alpha$-amine 2$\beta$-hydroxy-1$\beta$-[4-(benzoxazol-2-yl)benzyloxy]cyclopentyl-3$\alpha$-amine 2β-hydroxy-1β-[4-(benzoxazol-2-yl)benzyloxy]cycloheptyl-3α-amine 2α-hydroxy-1β-[4-(benzoxazol-2-yl)benzyloxy]cyclopentyl-3β-amine

EXAMPLE 14

When the above procedures are followed but the appropriate starting materials are used, then the desired compound may be obtained. A representative list of compounds which may be prepared include the following:

2-[4-(benzoxazol-2-yl)benzyloxy]cyclohexylamine
3-[4-(benzoxazol-2-yl)benzyloxy]cyclohexylamine
2-[4-(benzthiazol-2-yl)benzyloxy]cyclohexylamine
2-[3-(benzthiazol-2-yl)benzyloxy]cyclohexylamine
2-[4-(benzthiazol-2-yl)benzyloxy]cyclopentylamine
2-[4-benzoylbenzoxy]cyclohexylamine
2-[4-(3,4-methylenedioxy)benzyloxy]cyclohexylamine
2-[4-(2H-3,4-dihydro-1-benzopyran-6-yl)benzyloxy]cyclohexylamine
2-[4-(2,3-dihydrobenzofuran-5-yl)benzyloxy]cyclohexylamine
2-[4-(2,3-dihydro-1,4-benzodioxin-6-yl]benzyloxy]cyclohexylamine
2-[4-benzo[b]thien-2-yl)benzyloxy]cyclohexylamine
4-[4-(quinolin-2-yl)benzyloxy]cyclohexylamine
2-[4-(quinolin-2-yl)benzyloxy]cyclohexylamine
2-[4-(quinolin-2-yl)benzyloxy]cyclopentylamine
4-[4-napth-2-yl)benzyloxy]cyclohexylamine
4-[4-napth-1-yl)benzyloxy]cyclohexylamine
2-[4-napth-1-yl)benzyloxy]cyclohexylamine
4-[4-(1-methylindol-2-yl)benzyloxy]cyclohexylamine
2-[4-benzofuran-2-yl)benzyloxy]cyclohexylamine
4-[4-(3-methoxyphenyl)benzyloxy]cyclohexylamine
4-4-(3-methoxyphenyl)benzylthio]cyclohexylamine
2-[4-(2-(E)phenylethenyl)benzyloxy]cyclohexylamine
2-[4-(benzoxazol-2-yl)napth-1-yl]methoxycyclohexylamine
3-[5-(benzoxazol-2-yl)thien-2-yl]methoxycyclohexylamine
2-[5-(benzoxazol-2-yl)thien-2-yl]methoxycyclohexylamine
2-[4-(benzoxazol-2-yl)phenoxy]cyclohexylamine
2-[4-(benzoxazol-2-yl)phenethoxy]cyclohexylamine
4-[4-(benzthiazol-2-yl)benzylthio]cyclohexylamine
4-[4-(benzoylphenyl)phenethyl]cyclohexylamine
4-[4-(benzoylphenyl)benzyl]cyclohexylamine Various tests have been carried out to show the ability of the compounds of the present invention to exhibit pharmacological responses that can be correlated with activity in humans. These tests involve such factors as the effect of the compounds of Formula I to inhibit squalene synthesis. It has been found that compounds within the scope of this invention when tested using the following procedures show a marked activity for the inhibition of squalene synthase and hence are believed to be useful in the treatment of cholesterol-related disorders.

Squalene Synthase Inhibition Assay

The squalene synthase assay used is a modification of the procedures described by Popjak (1969) and Poulter et al. (1989):

Popjak, G. Enzymes of sterol biosynthesis in liver and intermediates of sterol biosynthesis. Meth. Enzymol. 15: 393–454, 1969.

Poulter, C. D., Capson, T. L., Thompson, M. D. and Bard R. S. Squalene synthase. Inhibition by ammonium analogues of carbocationic intermediates in the conversion of presqualene diphosphate to squalene. J. Am. Chem. Soc. 111: 3734–3739, 1989.

I. Animal Source and Tissue Preparation

Four male Sprague-Dawley rats weighing 100–120 gms are fed a low cholesterol rodent diet (#5012) obtained from Purina Mills, Inc. in Richmond, Ind.; and housed under reverse-light. Water is given ad lib. Rats are lightly anesthetized with ether and then decapitated. Livers are removed and enzymes are separated by the method described below.

II. Materials

Chemicals

All Chemicals are "A.C.S." in purity or better unless noted;

AquaSol®-2 scintillation fluid (NEF-952) (Du Pont/NEN Research Products, Boston, Mass.);

Anhydrous $MgCl_2$ (M-8266), β-NADPH tetrasodium salt, reduced form (N-1630), Bovine serum albumin (A-6003), Cholesterol (C-8503);

Squalene (S-3626), (Sigma Chemical Co., St. Louis, Mo.);

Bio-Rad protein assay dye concentrate (Bio-Rad Laboratories, Richmond, Calif.);

Denatured ethanol, DMSO, HCl (1 N), KOH, methanol, NaOH (0.1N, 1N), petroleum ether (M-280 grade), potassium phosphate dibasic, 2-propanol (Fisher Scientific, Pittsburgh, Pa.);

Zero grade nitrogen gas mixture (certified analysis) (Woodland Oxygen & Supply Co., Philadelphia, Pa.).

Radiochemicals:

[1-$^3$H(N)]-FPP, triammonium salt (NET-1042), (Du Pont/NEN, Boston, Mass.);

[4, 8, 12, 13, 17, 21-$^3$H]-Squalene (NET-645) (Du Pont/NEN);

Non-radiolabeled FPP is prepared in-house. The solid FPP is aliquoted and stored at −80° C. FPP is dissolved in 70% ethanol/30% 0.25 M $NH_4 HCO_3$ at the concentration of 10 mM and the solution is aliquoted (200 μl each) and stored at −80° C.

III. Preparation of Assay Substances

A) Test Solutions

Test solutions are prepared fresh in 100% DMSO or $dH_2O$. Subsequent dilutions are made in the same solvent. Compounds are tested initially at 1 or 10 μM (final concentrations).

B) Assay Buffer

Potassium Phosphate (50 mM, 8.71 g/l) pH 7.5 stock buffer is prepared and stored at 4° C. until use. Anhydrous $MgCl_2$ is added to the phosphate buffer on the day of assay for a final concentration of 10 mM (95 mg/100 ml). The buffer is flushed with $N_2$ before use.

C) Substrate

Non-radiolabeled FPP is diluted to 50 μM (100 μl 10 mM cold FPP +19.9 ml phosphate buffer). Then, 14 μl (20×10$^6$ dpm) of $^3$H-FPP (0.5 mCi/ml, 0.011 mg/ml) is added. 200 μl of this mixture is added per assay tube for a final reaction concentration of 10 μM FPP (~200,000 dpm/assay tube).

D) β-NADPH Solution 37.5 mg of β-NADPH is added to 9 ml assay buffer for a 5 mM concentration of β-NADPH. The mixture is vortexed and 100 μl of this solution is added to each tube for a final assay concentration of 0.5 mM β-NADPH.

E) KOH in Ethanol 75 gm of KOH is dissolved in 500 ml of denatured ethanol for a 15% solution and stored at 0° C. until use. 1 ml of this solution is added per tube to terminate the reaction.

IV. Experimental Procedure

A) Enzyme Preparation:

Immediately following decapitation, livers are removed one at a time from four rats. The livers are combined and weighed in a tared beaker. Assay buffer is added equal to three times the liver weight. The liver is first homogenized with a blender for thirty seconds, and then by a motor driven teflon pestle at a speed of 2.5. During homogenization, the liver is kept on ice. When the liver is fully homogenized, the homogenate is centrifuged at 10,000 g for 30 min at 4° C. in 50 ml capacity centrifuge tubes. The mitochondrial pellet is discarded and the supernatant is filtered through a layer of gauze moistened with a little buffer. This supernatant is recentrifuged at 105,000 g for one hour at 0° C. in an ultracentrifuge in 25 ml capacity ultracentrifuge tubes.

Following centrifugation, the supernatant is removed and discarded. The sediment pellet consists of 2 layers: a transparent inner layer of glycogen, surrounded by an opaque brown layer of microsomes. The brown outer microsomal layer is carefully removed with a spatula and placed in a beaker on ice. Assay buffer is added in an amount equal to one half the original homogenate volume, and this mixture is poured into ultracentrifuge tubes. These tubes are recentrifuged at 105,000 g for 1 hour at 4° C.

After this centrifugation is complete, the supernatant is again removed and discarded. Fresh assay buffer is added to the combined pellets to achieve a volume equal to one tenth of the original homogenate volume. The microsomal fraction is then rehomogenized on a motor driven teflon pestle at a speed of 2.5 to partially solubilize and make a uniform suspension of the microsomes. The enzyme (~20 ml, ~40 mg protein/ml) is aliquoted (200 μl) into eppendorf plastic tubes, capped and stored at −80° C. until use.

B) Assay Procedure

To begin the assay, 20 μl of the compound of this invention or vehicle solution is added to each 16×150 screw-cap culture tube on ice. Then 580 μl of $N_2$ flushed assay buffer is pipetted into each tube. 100 μl of cofactor is next added to each tube, followed by 100 μl of a dilution of microsomal enzyme (approximately 80 ug protein). The tubes are preincubated for 10 minutes at 37° C., and 200 μl of the $^3$H-FPP (200,000 dpm, 10 μM final conc.) is added to each tube at two second intervals. The tubes are then incubated for exactly 10 minutes, shaking at 150 oscillations per minute. After the 10 minute incubation, the reaction is stopped by the addition of 1 ml of 15% KOH in ethanol, and the tubes are incubated for 30 minutes in a 65° C. water bath for saponification of lipids and solubilization of proteins. The tubes are cooled on ice for five minutes. The samples are next extracted with 5 ml of petroleum ether by shaking for 10 minutes at low speed on a metabolic shaker. Each lower aqueous layer is frozen in a dry ice/alcohol bath (2-propanol/methanol, 1:1), and each organic layer is poured into another set of 16×150 screw-top culture tubes containing 2 ml of deionized water. Each ether layer is washed by vortexing each tube for 5 seconds. The aqueous layers are again frozen in the dry ice/alcohol bath, and the ether is poured into scintillation vials. 10 ml of AquaSol ® is next added to each vial, and the vials are counted for 5 minutes in a scintillation counter. Percent inhibitions are calculated from the counts obtained.

V. Statistical Considerations

The samples are counted as dpm using a Beckman Scintillation counter (Model LS-9000). Percent inhibition is calculated using a Lotus 1-2-3 program. The $IC_{50}$ values are calculated using a linear regression program of Tallarida and Murray (1987). Tallarida, R. J. and Murray, R. B. Manual of pharmacologic calculations with computer programs. Springer-Verlag, 1987.

The following in vivo assays are used to determine the effectiveness of compounds of this invention to inhibit squalene synthase.

In Vivo Rat Method

Forty male Sprague-Dawley rats weighing 80-90 gms are fed a low cholesterol rodent meal diet (#5012) obtained from Purina Mills, Inc. in Richmond, Indiana; and housed under reversed-light. Water is given ad lib. After a week of housing, the rats are fed cholestyramine (2% in diet) for the next 2 days. One day after the cholestyramine treatment, a compound is given three times to 4 rats (30 mg/kg, in 10 ml 0.5% methylcellulose/Kg, p.o.) at 8 a.m., 5 p.m. and 8 a.m. the following day. Four hours after the last dose, the rat is decapitated and blood and the liver are collected. Serum is separated and analyzed for cholesterol by an assay kit supplied by Sigma Chemical Co., St. Louis, Mo. Sterols in the serum and the liver are also analyzed by HPLC analysis. The liver cholesterol level is determined by quantitating against cholesterol as a standard by HPLC. Results are determined as the change in the liver and serum cholesterol compared to respective vehicle treated control values.

Mouse in vivo assay for cholesterol-lowering effect

Balb-c mice weighing 20-25 gms are used for this study. Mice are fed a meal diet (RP#5012) containing 2% cholestyramine. Test compound is dissolved/suspended in 0.5% methyl cellulose and given to mice at 50 mg/kg, b.i.d. (n=8). Blood is collected from the tail on days 0 and 7 and from inf. vena cava on day 14. Body weights and the food consumption are monitored weekly. Serum cholesterol is determined by an enzyme assay kit (Sigma Chemical Co.). Serum and the liver are analyzed by HPLC for various sterols. Results are determined as % change from the vehicle treated controls.

HPLC Procedure

Sample preparation

In 16×25 mm screw cap glass tubes, is added 0.5 ml serum or plasma or liver slices suspension (0.11 gm/ml buffer). To this is then added 1 ml of KOH/ethanol (15%). The glass tubes are incubated at 80° C. for 2 hours while shaking. After saponification, 10 ml petroleum ether is added to each tube and then capped. The tubes are shaken for 30 min. then frozen at −80° C. and the ether removed to 16×50 mm screw top glass tubes. Water (2 ml) is added and again the tubes are shaken for 10 minutes. After freezing, the ether is transfered into 16×25 mm glass culture tubes. The ether is evaporated under $N_2$. HPLC grade ethanol (0.5 ml) is added to the tubes, capped and shaken for 30 min to dissolve all lipids. The ethanol is filtered using a syringe filter (pore size:0.45 uM, Spartan-13, Schleicher & Schuell) and 50 ul of this solution is injected into HPLC.

HPLC specifications

Column: Partisil110 ODS-3, C-18 reversed phase, 25 cm length at 25° C. [Whatman Cat#4228-001]
Pump: Waters 6000A, Isocratic system
Solvent: Acetonitrile:water:: 95:5; 2 ml/min
Run Time: 33 min
50 ul injection by Autosampler WISP 710B, Waters/Millipore
Wavelength:210 rim, Applied Biosystems 757 Absorbance detector
Integrator: Hewlett Packard 3396 Series II.

Typical Retention Times

Squalene dioxide—7.5 min
Squalene oxide—14 min
7-dehydro Chol.—16 min
Cholesterol—23 min
Squalene—30 min Compounds within the scope of Formula I have been tested by the foregoing assay procedures and exhibit marked squalene synthase inhibition activity and are useful as hypocholesterolemic or hypolipidemic agents by virtue of their ability to inhibit the biosynthesis of cholesterol. Having such ability, the compounds are incorporated into pharmaceutically acceptable carriers and administered to a patient in need of such cholesterol biosynthesis inhibition. These pharmaceutical formulations contain at least one compound according to this invention.

Treatment with a combination of an HMG-CoA reductase inhibitor and a squalene synthase inhibitor would have a synergistic effect on inhibiting cholesterol biosynthesis. Inhibiting the squalene synthase enzyme and the HMG-CoA reductase enzyme at the same time would most closely resemble the physiological conditions of cholesterol homeostasis. A squalene synthase inhibitor could keep cellular concentrations of farnesyl diphosphate high enough for the synthesis of the small amounts of dolichol, ubiquinone, and the farnesylated proteins required by the cell. This would maintain some feedback regulation of the HMG-CoA reductase enzyme and allow smaller amounts of the HIVIG-CoA reductase inhibitor to be used.

Other combinations with a squalene synthase inhibitor which could have a synergistic effect for controling undersirable cholesterol levels in the body include niacin, antihyperlipoproteinemic agents such as gemfibrozil, cholesterol absorption inhibitors, bile acid sequestrants, antioxidants and lipoxygenase inhibitors.

The compounds of the present invention can be administered to a mammalian host in a variety of forms adapted to the chosen route of administration, i.e., orally, or parenterally. Parenteral administration in this respect includes administration by the following routes: intravenous, intramuscular, subcutaneous, intraocular, intrasynovial, transepithelially including transdermal, opthalmic, sublingual and buccal; topically including opthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens a preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent of dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimersal, and the like. In many cases, it will be preferable to include isotonic agents, for example, sugars or sodium chloride. Prolonged absorption of the injectable compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and it will vary with the form of administration and the particular compound chosen, and also, it will vary with the particular patient under treatment. He will generally wish to initiate treatment with small dosages by small increments until the optimum effect under the circumstances is reached. The therapeutic dosage will generally be from about 0.1 to about 100 mg/kg/dy, and preferably from about 10 mg to about 1000 mg day, or from about 0.1 mg to about 50 mg/kg of body weight per day and preferably from about 0.1 to about 20 mg/kg of body weight per day and may be administered in several different dosage units. Higher dosages on the order of about 2× to about 4× are required for oral administration.

We claim:

1. A compound of the formula:

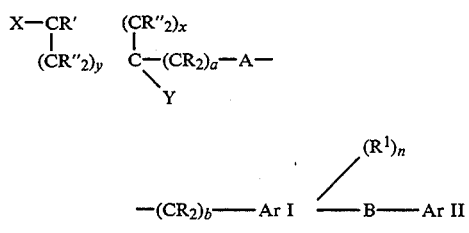

where:
Ar I is phenylene;
Ar II is benzoxazolyl;
A is O, S, NR, SO, $SO_2$, NR—C=O, O=C—NR, RC=CR, C≡C or a bond;
B is $(CR_2)_e$, O, S, NR, O=C, SO, $SO_2$ or a bond;
one of X or Y is R''';
one of X or Y is $H_2N$—$(CR_2)_z$—;
a and b are independently 0–4 and a+b=0–4;
e is 1–2;
m and n are independently 0–2;
x is 1–6;
y is 0–2;
x+y is 1–6;
z is 0–3;
R' is hydrogen, $C_{1-6}$-alkyl or hydroxy;
R'' is hydrogen, $C_{1-6}$-alkyl or hydroxy;
R''' is hydrogen, $C_{1-6}$-alkyl, hydroxy or carboxy;
one set of vicinal R'' and R''' groups may form a double bond when x+y=3–6;
R is hydrogen or $C_{1-6}$-alkyl;
$R^1$ and $R^2$ are independently hydrogen, $C_{1-6}$-alkyl, $C_{1-6}$-alkoxy, hydroxy, chloro, fluoro, bromo, trifluoromethyl, amino or mono-or di-$C_{1-6}$-alkylamino; and
its stereoisomers, enantiomers, diastereoisomers and racemic mixtures; or a pharmaceutically acceptable salt thereof.

2. A compound according to claim 1 of the formula:

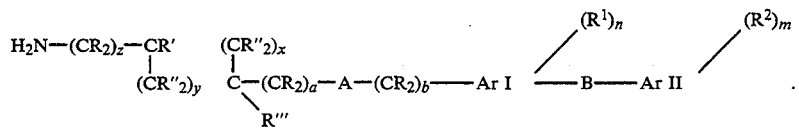

3. A compound according to claim 1 of the formula:

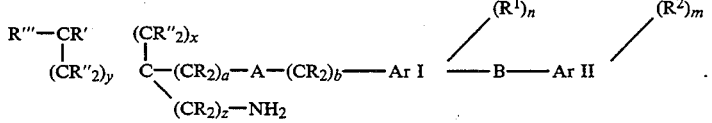

4. A compound according to claim 2 where:
Ar I is phenylene and
Ar II is benzoxazolyl
where:
$R^1$ and $R^2$ are independently hydrogen, $C_{1-6}$-alkyl, $C_{1-6}$-alkoxy, hydroxy, chloro, fluoro, bromo, trifluoromethyl;
$R^3$ and $R^4$ together are O—$CH_2$—$CH_2$, O—$CH_2$—$CH_2$—$CH_2$, O—$CH_2$—O or O—$CH_2$—$CH_2$—O;
R' is hydrogen, $C_{1-6}$-alkyl or hydroxy;
R'' is hydrogen, $C_{1-6}$-alkyl or hydroxy; and
R''' is hydrogen, $C_{1-6}$-alkyl, hydroxy or carboxy.

5. A compound according to claim 3 where:
Ar I is phenylene and
Ar II is benzoxazolyl
where:
$R^1$ and $R^2$ are independently hydrogen, $C_{1-6}$-alkyl, $C_{1-6}$-alkoxy, hydroxy, chloro, fluoro, bromo, trifluoromethyl;

$R^3$ and $R^4$ together are O—CH$_2$—CH$_2$, O—CH$_2$—CH$_2$—CH$_2$, O—CH$_2$—O or O—CH$_2$—CH$_2$—O;

R' is hydrogen, C$_{1-6}$-alkyl or hydroxy;

R" is hydrogen, C$_{1-6}$-alkyl or hydroxy; and

R'" is hydrogen, C$_{1-6}$-alkyl, hydroxy or carboxy.

6. A compound according to claim 4 of the formula $$H_2N-(CR_2)_z-CR' \quad (CR''_2)_x$$
$$(CR''_2)_y \quad C-(CR_2)_a-A-(CR_2)_b-\text{[phenyl}(R^1)_n]-B-\text{[benzoxazol}(R^2)_m]$$
$$\quad R'''$$

where:

A is O, S, NR, CH=CH or a bond;

B is (CR$_2$)$_e$, O=C, O, S, NR or a bond;

a and b are independently 0–3 and a+b=0–3;

e is 1–2;

m and n are independently 0–2;

x is 1–6;

y is 0–2;

x+y is 1–6;

z is 0–3;

R' is hydrogen, C$_{1-6}$-alkyl or hydroxy;

R'" is hydrogen, C$_{1-6}$-alkyl, hydroxy or carboxy; R" is hydrogen, C$_{1-6}$-alkyl or hydroxy;

one set of vicinal R" and R'" groups may form a double bond when x+y=3–6;

R is hydrogen or C$_{1-6}$-alkyl; and

R$^1$ and R$^2$ are independently hydrogen, C$_{1-6}$-alkyl, C$_{1-6}$-alkoxy, hydroxy, chloro, fluoro, bromo or trifluoromethyl.

7. A compound according to claim 5 of the formula $$R''''-CR' \quad (CR''_2)_x$$
$$(CR''_2)_y \quad C-(CR_2)_a-A-(CR_2)_b-\text{[phenyl}(R^1)_n]-B-\text{[benzoxazol}(R^2)_m]$$
$$\quad (CR_2)_z-NH_2$$

where:

A is CH=CH, O, S, NR or a bond;

B is (CR$_2$)$_e$, O=C, O, S, NR or a bond;

a and b are independently 0–3 and a+b=0–3;

e is 1–2;

m and n are independently 0–2;

x is 1–6;

y is 0–2;

x+y is 1–6;

z is 0–3;

R' is hydrogen, C$_{1-6}$-alkyl or hydroxy;

R" is hydrogen, C$_{1-6}$-alkyl or hydroxy;

R'" is hydrogen, C$_{1-6}$-alkyl, hydroxy or carboxy;

one set of vicinal R" and R'" groups may form a double bond when x+y=3–6;

R is hydrogen or C$_{1-6}$-alkyl; and

R$^1$ and R$^2$ are independently hydrogen, C$_{1-6}$-alkyl, C$_{1-6}$-alkoxy, hydroxy, chloro, fluoro, bromo or trifluoromethyl.

8. A compound according to claim 6 where:

A is O or a bond;

B is a bond;

a is 0–1;

b is 0–1;

m and n are independently 0–1;

x is 1–6;

y is 0–2;

x+y is 1–6;

z is 0–1;

R, R', R", R'" and R$^1$ are hydrogen or hydroxy; and

R$^2$ is hydrogen, C$_{1-6}$-alkyl, C$_{1-6}$-alkoxy or chloro, fluoro or bromo.

9. A compound according to claim 7 where:

A is O or a bond;

B is a bond;

a is 0–1;

b is 0–1;

m and n are independently 0–1;

x is 1–6;

y is 0–2;

x+y is 1–6;

z is 0–1;

R, R', R", R'" and R$^1$ are hydrogen or hydroxy; and

R$^2$ is hydrogen, C$_{1-6}$-alkyl, C$_{1-6}$-alkoxy or chloro, fluoro or bromo.

10. A compound according to claim 6 which is trans-2-[4-(benzoxazol-2-yl)benzyloxy]cyclohexylamine or a pharmaceutically acceptable salt thereof.

11. A compound according to claim 6 which is cis-2-[(4-benzoxazol-2-yl)benzyloxy]cyclohexylamine or a pharmaceutically acceptable salt thereof.

12. A compound according to claim 6 which is trans-2-amino-[4-(benzoxazol-2-yl)benzyloxy]cyclopentane or a pharmaceutically acceptable salt thereof.

13. A compound according to claim 6 which is trans-2-(4-[benzoxazol-2-yl]benzyloxy)cycloheptylamine or a pharmaceutically acceptable salt thereof.

14. A compound according to claim 7 which is 2α-hydroxy-3β[(4-benzoxazol-2-yl)benzyloxy]cyclohexyl-1β-amine or a pharmaceutically acceptable salt thereof.

15. A compound according to claim 7 which is 2β-hydroxy-3β[(4-benzoxazol-2-yl)benzyloxy]cyclohexyl-1α-amine or a pharmaceutically acceptable salt thereof.

16. A compound according to claim 7 which is 1-amino-[4-(benzoxazol-2-yl)benzyloxymethyl]cyclopentane or a pharmaceutically acceptable salt thereof.

17. A method of lowering or maintaining reduced cholesterol levels in a patient requiring such treatment which comprises administering to such patient a squalene synthase inhibitor effective amount of a compound of the formula according to claim 1.

18. A method for inhibiting cholesterol biosynthesis which comprises administering to a patient in need of such inhibition a squalene synthase inhibiting effective amount of a compound according to claim 1.

19. A method according to claim 18 where the patient is in need of a hypocholesterolemic or hypolipidemic agent.

20. A method according to claim 19 for treating atherosclerosis.

21. A pharmaceutical composition comprising a squalene synthetase inhibitor effective amount of a compound according to claim 1 in admixture with a pharmaceutical carrier.

22. A pharmaceutical composition according to claim 21 which further includes an HMG CoA reductase inhibitor.

* * * * *